(12) United States Patent
Wölfle et al.

(10) Patent No.: US 9,617,238 B2
(45) Date of Patent: *Apr. 11, 2017

(54) 2-OXO-1,3-DIOXOLANE-4-CARBOXAMIDE BUILDING BLOCKS, THEIR PREPARATION AND USE

(71) Applicant: Construction Research & Technology GmbH, Trostberg (DE)

(72) Inventors: Heimo Wölfle, Traunstein (DE);
Burkhard Walther, Taching am See (DE); Sophie Putzien, Ampfing (DE)

(73) Assignee: Construction Research & Technology GmbH, Trostberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/760,834

(22) PCT Filed: Jan. 30, 2014

(86) PCT No.: PCT/EP2014/051784
§ 371 (c)(1),
(2) Date: Jul. 14, 2015

(87) PCT Pub. No.: WO2014/118268
PCT Pub. Date: Aug. 7, 2014

(65) Prior Publication Data
US 2015/0353521 A1  Dec. 10, 2015

(30) Foreign Application Priority Data

Jan. 31, 2013 (EP) .................................. 13153383

(51) Int. Cl.
*C07D 317/38* (2006.01)
(52) U.S. Cl.
CPC ................................ *C07D 317/38* (2013.01)
(58) Field of Classification Search
CPC .................................................. C07D 317/38
See application file for complete search history.

(56) References Cited

U.S. PATENT DOCUMENTS

| 7,968,572 | B2 | 6/2011 | Nakai et al. |
| 8,044,194 | B2 | 10/2011 | Dubois et al. |
| 2010/0317838 | A1 | 12/2010 | Dubois et al. |
| 2011/0313177 | A1 | 12/2011 | Mecfel-Marczewski et al. |
| 2014/0228583 | A1 | 8/2014 | Mecfel-Marczewski et al. |

FOREIGN PATENT DOCUMENTS

| EP | 0 001 088 A1 | 3/1979 |
| EP | 1 941 946 A1 | 7/2008 |
| EP | 2 397 474 A1 | 12/2011 |
| JP | 7-285960 A | 10/1995 |
| JP | 2006003433 A | 1/2006 |

| JP | WO 2007040208 A1 * | 4/2007 | ............ A61K 31/00 |
| WO | WO 2004/003001 A1 | 1/2004 | |
| WO | WO 2007/040208 A1 | 4/2007 | |

(Continued)

OTHER PUBLICATIONS

PCT/EP2011/058945—International Search Report, mailed Nov. 15, 2011.
PCT/EP2011/058945—International Written Opinion, mailed Nov. 15, 2011.
PCT/EP2011/058945—International Preliminary Report on Patentability, mailed Jul. 27, 2012.
PCT/EP2012/072589—International Search Report, mailed on Jan. 4, 2013.
PCT/EP2012/072589—International Written Opinion, mailed on Jan. 4, 2013.
PCT/EP2012/072589—International Preliminary Report on Patentability, mailed on Jun. 24, 2014.

(Continued)

*Primary Examiner* — Samantha Shterengarts
*Assistant Examiner* — Matt Mauro
(74) *Attorney, Agent, or Firm* — Curatolo Sidoti Co., LPA; Joseph G. Curatolo; Salvatore A. Sidoti

(57) ABSTRACT

The present invention suggests a 2-oxo-1,3-dioxolane-4-carboxamide of formula (I),

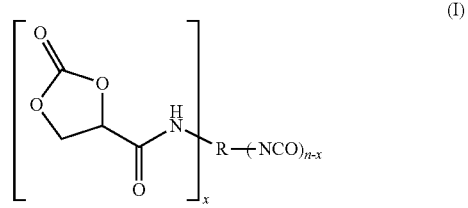

wherein R is an n-valent radical, n is an integer from 2 to 4, preferably from 2 to 3, and x is an integer from 1 to n−1. The invention furthermore suggests a process for the preparation of the 2-oxo-1,3-dioxolane-4-carboxamide of formula (I) from 2-oxo-1,3-dioxolane-4-carboxylic acid of formula (II)

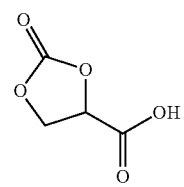

with a polyisocyanate of the formula $R(NCO)_n$, where R and n have the meanings given, the use of the 2-oxo-1,3-dioxolane-4-carboxamide of formula (I) for the preparation of a 2-oxo-1,3-dioxolane-4-carboxamide-substituted prepolymer, and the 2-oxo-1,3-dioxolane-4-carboxamide-substituted prepolymer thus obtainable.

8 Claims, No Drawings

(56) References Cited

FOREIGN PATENT DOCUMENTS

| WO | WO 2011/157551 A1 | 12/2011 |
|---|---|---|
| WO | WO 2012/065879 A1 | 5/2012 |
| WO | WO 2013/092011 A1 | 6/2013 |

OTHER PUBLICATIONS

PCT/EP2014/051784—International Search Report, mailed on Mar. 5, 2014.
PCT/EP2014/051784—International Written Opinion, mailed on Mar. 5, 2014.
Tomita, et al., "Model Reaction for the Synthesis of Polyhydroxyurethanes from Cyclic Carbonates with Amines: Substituent Effect on the Reactivity and Selectivity of Ring-Opening Direction in the Reaction of Five-Membered Cyclic Carbonates with Amine", Journal of Polymer Science, 2001, vol. 39, pp. 3678-3685, John Wiley & Sons Inc.
Lewis, et al., "Synthesis of L-660,631 Methyl Ester and Related Compounds", Tetrahedron Letters, Jan. 1, 1988, vol. 29, No. 19, pp. 2279-2282, Pergamon Press PLC, Great Britain.
Diakoumakos, Constantino, et al., "Non-Isocyanate-Based Polyurethanes Derived upon the Reaction of Amines with Cyclocarbonate Resins", Macromol. Symp., 2004, vol. 216, pp. 37-46.
Petit, Y., et al., "Ethyl Glycidate From (S)-Serine: Ethyl (R)-(+)-2,3-Epoxypropanoate", Organic Synthesis Collection, 2004, vol. 10, p. 401; Organic Syntheses, 1998, vol. 75, p. 37.
Stevenson, Christian P., et al., "Preparation of (S)-Methyl Glycidate VIA Hydrolytic Kinetic Resolution", Organic Syntheses, 2006, vol. 83, pp. 162-169; Organic Syntheses Collection, 2009, vol. 11, pp. 157-163.
PCT/EP2014/051784—International Preliminary Report on Patentability, mailed on Aug. 4, 2015.

* cited by examiner

2-OXO-1,3-DIOXOLANE-4-CARBOXAMIDE BUILDING BLOCKS, THEIR PREPARATION AND USE

CROSS REFERENCE TO RELATED APPLICATIONS

This application is a national stage application of International Application No. PCT/EP2014/051784, filed Jan 30, 2014, which claims priority from European Patent Application No. 13153383.8, filed Jan. 31, 2013, which are incorporated herein by reference.

The present invention relates to a 2-oxo-1,3-dioxolane-4-carboxamide of formula (I),

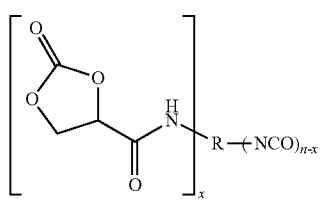

(I)

wherein R is an n-valent radical, n is an integer from 2 to 4, preferably 2 to 3, and x is an integer from 1 to n−1, to a process for the preparation of a 2-oxo-1,3-dioxolane-4-carboxamide of formula (I) by reaction of 2-oxo-1,3-dioxolane-4-carboxylic acid of formula (II)

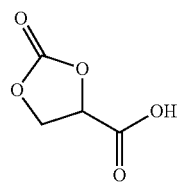

(II)

with a polyisocyanate of the formula $R(NCO)_n$, where R and n have the meanings given, to the use of a 2-oxo-1,3-dioxolane-4-carboxamide of formula (I) for the preparation of a 2-oxo-1,3-dioxolane-4-carboxamide-substituted prepolymer and to said 2-oxo-1,3-dioxolane-4-carboxamide-substituted prepolymer thus obtainable.

Structurally similar compounds are described in our International patent application WO 2013/092011 A1 with priority of 22.12.2011, published 27 Jun. 2013, describing 2-oxo-1,3-dioxolane-4-carboxamides of formula (III),

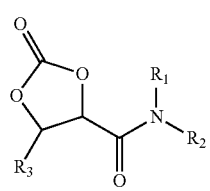

(III)

in which $R_2$ can be, inter alia, an n-valent radical (n>1) which is substituted with n−1 further 2-oxo-1,3-dioxolane-4-carboxamide groups of general formula (IV),

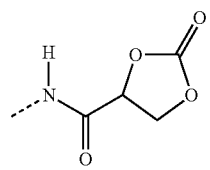

(IV)

processes for the preparation of these 2-oxo-1,3-dioxolane-4-carboxamides, processes for the preparation of the 2-oxo-1,3-dioxolane-4-carboxylic acids of formula (V),

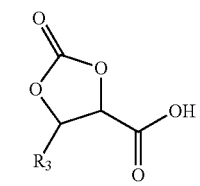

(V)

and the use of said 2-oxo-1,3-dioxolane-4-carboxamides for the preparation of (poly)-hydroxyurethanes. However, PCT/EP2012/072589 does not describe the compounds according to the present invention having —NCO groups in the molecule.

WO 2004/003001 A1 describes compounds of the general formula (VI)

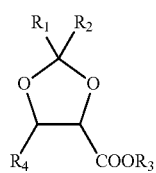

(VI)

where $R_1$ and $R_2$ may be radicals independent of one another, $R_1+R_2=O$ or $CR_1+R_2$ may be a 3-6-membered cycloalkyl group. $R_4$ may be hydrogen, straight-chain or branched $C_{1-8}$-alkyl, $C_{5-12}$-cycloalkyl or $C_{6-15}$-aryl. $R_3$ may be straight-chain or branched $C_{1-8}$-alkyl or $C_{6-15}$-aryl. In general, WO 2004/003001 A1 describes the enzymatic racemate separation of the enantiomers of type (VI) but without indicating a synthesis for these compounds.

EP 1941946 A1 describes the use of a carbonitride catalyst inter alia for the preparation of certain disubstituted organic carbonates. These may also be compounds of the general formula (VII),

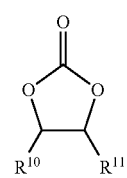

(VII)

where $R^{10}$ and $R^{11}$, independently of one another, are selected optional substituents. Possible meanings of the substituents are alkyl, aryl, herteroaryl and ester groups CO$_2$A, where A may in turn be alkyl or aryl, e.g. straight-chain or branched C$_{1-6}$-alkyl, preferably C$_{1-3}$-alkyl and particularly preferably methyl or ethyl. However, no syntheses for 2-oxo-1,3-dioxolane systems are stated.

JP 2006-003433 A discloses a sealing composition for liquid crystal display elements which comprises a compound of the general formula (VIII),

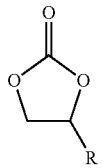
(VIII)

where R is H, a hydroxyl group, a cyano group, a carboxylic acid group, an optionally substituted aromatic ring, a straight-chain, branched or cyclic alkyl group, an acyl group or an ester group. The 2-oxo-1,3-dioxolane-4-carboxylic acid (R=COOH) is also men-tioned.

EP 0001088 A1 describes inter alia 2-oxo-1,3-dioxolanes of the general formula (IX), where R can be H or CH$_3$.

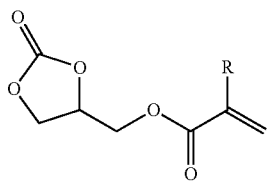
(IX)

EP 2397474 A1 describes 2-oxo-1,3-dioxolane-4-carboxylic acid esters of formula (X)

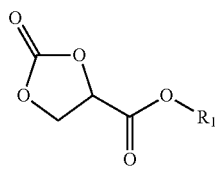
(X)

in which R$_1$ may be inter alia Me or Et or an n-valent radical which may be substituted with a maximum of n−1 further 2-oxo-1,3-dioxolane-4-carboxyl groups, a process for their preparation by means of carboxylation of the corresponding epoxides, a process for their transesterification, and also their use for the preparation of hydroxyurethanes and as end groups for the blocking of amines.

US 2010/0317838 A1 describes compounds of formula (XI)

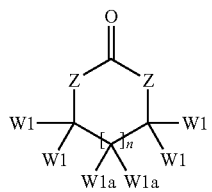
(XI)

in which Z=O and n=0, at least one of the radicals W1 or W1a comprises a protected glycoside, and each of the radicals W1 and W1a, independently of one another, may inter alia also be an amide group.

Polyurethanes based on polyisocyanates are a widely applied polymer family. These polymers are used for shoes, mattresses, automotive parts, sports equipment, artificial leather and the like. Also in construction chemistry they are one of the most widely applied materials e.g. for sealants, adhesives, coatings and foams in areas like mining, roofing, flooring, tile fixing, and waterproofing, to name a few. The high resistance to acids, alkalis and chemicals of the cured compositions obtained in this way are advan-tageous. However, monomeric low molecular weight isocyanate compounds are inher-ently toxic and sensitizing. The grade of toxicity correlates directly with the volatility of the monomers. In closed industrial production processes (e.g. shoes, foams, formed parts etc.) these facts play a minor role, but when it comes to applications where curing is performed openly, health issues rise great concerns about the use of isocyanates especially in do-it-yourself and spray applications. Therefore a considerable amount of work was invested by industry and academia to avoid the use of isocyanates to obtain polyurethanes.

The most promising way is the ring opening of cyclic carbonates with amines to yield hydroxyurethanes. Cyclic carbonate compounds are toxicologically acceptable. Thus, for instance, glycerol carbonate (4-(hydroxymethyl)-2-oxo-1,3-dioxolane) is regularly used in cosmetics.

Cyclic carbonate compounds react with amines with ring opening inter alia to give hydroxyurethanes (cf. formula scheme below):

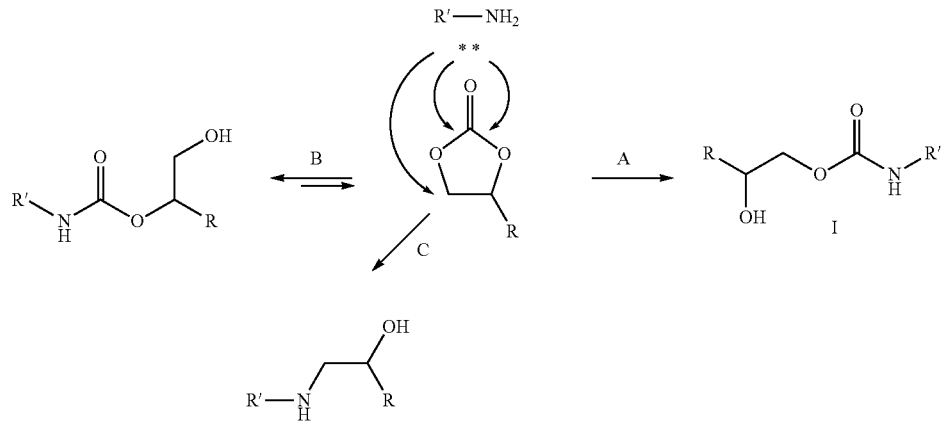

Disadvantages of the systems based on glycerol carbonate are the low regioselectivity, which leads to reaction pathways A, B and C, the comparatively low reactivity of the systems at room temperature, and the fact that catalysts which increase the rate of the ring opening obviously also promote the back-reaction, which can lead to a partial decomposition of the products already formed.

In the aforementioned EP 2397474 A1, these problems have been partially solved by using an ester group instead of an ether group in R. This electron-withdrawing group led to a considerable increase in the rate of the reaction and to a preference for reaction pathway A. In the case of the secondary hydroxyurethanes [I] formed, no back-reaction was observed. However, the production of binders which comprise two or more 2-oxo-1,3-dioxolane-4-carboxyl groups in the molecule is difficult since this takes place via a transesterification, during which the cyclocarbonate ring can also be attacked.

The aforementioned US 2010/0317838 A1 gives the impression that this ring opening reaction is independent of the nature of R (cf. claim 17 of US 2010/0317838 A1 which is directed to the ring opening of compounds of claim 1 which may contain ester groups or amide groups alike). However, this impression is quite misleading.

Firstly, studies have been carried out (cf. H. Tomita, F. Sanda, T. Endo, Journal of Polymer Science: Part A: Polymer Chemistry, Vol. 39, 3678-3685 (2001)) according to which the reactivity of the 2-oxo-1,3-dioxolanes, which are substituted in 4-position with the group R, with amines increases in the order: R=Me<R=H<R=Ph<R=CH$_2$OPh<<R=CF$_3$.

Secondly, in the case of the products of the aforementioned EP 2397474 A1 where the polymeric main chain is attached through ester bonds, i.e. R in the formula scheme below means the polymeric main chain, the ring opening (hardening) reaction is accom-panied by a certain amount of aminolysis of the ester bond leading to the detachment of the main chain in the form of an unreactive alcohol.

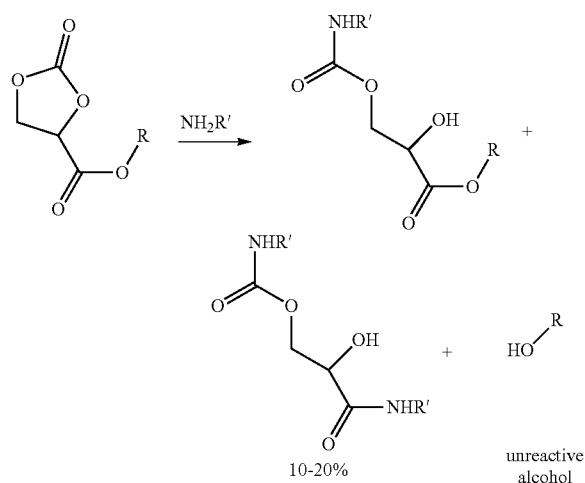

In the aforementioned PCT/EP2012/072589, this problem has been partially solved by using an amide group instead of an ester group. These compounds are obtained by reacting 2-oxo-1,3-dioxolane-4-carboxylic acids with suitable isocyanates. In the case of the amides thus formed aminolysis is per se not possible. If any transamination occurred, the formed amine would be capable of acting as a reactive hardener to attack further cyclic carbonate groups. Cross-linking and hardening of the products are thus much higher (cf. the formula scheme):

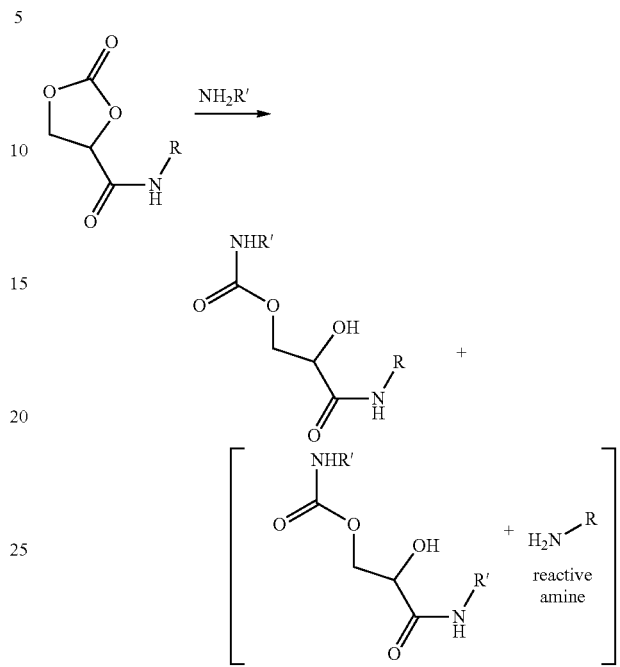

However, due to the limited number of commercially available polyisocyanates the synthesis of binders is quite limited. More flexibility in binder synthesis would be highly de-sirable. It has thus been the technical problem underlying the present invention to pro-vide alternative 2-oxo-1,3-dioxolane-4-carboxamides having —NCO groups in the molecule, which can be used for the preparation of 2-oxo-1,3-dioxolane-4-carboxamide-substituted prepolymers.

The present invention thus provides a 2-oxo-1,3-dioxolane-4-carboxamide of formula (I),

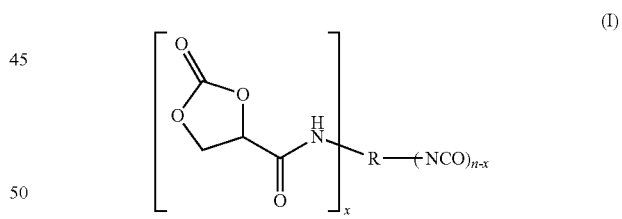

wherein R is an n-valent radical, n is an integer from 2 to 4 and x is an integer from 1 to n−1. These compounds of the present invention are to be called "building blocks" since it is possible to use them for the preparation of 2-oxo-1,3-dioxolane-4-carboxamide-substituted prepolymers through reaction with usual polyols.

For the purpose of the present invention, the term "n-valent radical" generally means that R is a group which is substituted with n substituents. In other words, R is a group which has a valency of "n".

According to a preferred embodiment, n can be an integer from 2 to 3. From a formal point of view, R would be a n-valent polyisocyanate after the abstraction of the —NCO groups. In this context the term "abstraction" does not refer to a chemical operation but simply to formally taking away the —NCO groups from a chemical formula of a polyisocyanate. In case that n is equal to 2 or 3, x is equal to 1 or 2.

Said polyisocyanate can be an aliphatic polyisocyanate, an aromatic polyisocyanate or a combined aliphatic/aromatic polyisocyanate with an —NCO functionality (number of —NCO groups in the molecule) of n=2 to 4, preferably n=2 to 3.

For the purposes of the present invention, the polyisocyanates according to the invention are also intended to include dimers (uretdiones) and trimers (isocyanurates). Particular importance is attributed here to the HDI trimer. Furthermore, oligomers are also to be included, such as e.g. "polymeric MDI" where o=0 to 2:

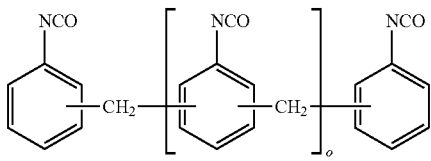

On the other hand, also polymeric MDI wherein o=0 to 10 is contemplated in the present invention.

Moreover, prepolymers of polyisocyanates with polyols can also be used if a stoichio-metric excess of NCO groups is present. Suitable polyols include polyoxyalkylene polyols (also called "polyether polyols"), which can contain inter alia ethylene oxide units, propylene oxide units and butylene oxide units, aliphatic diols and polyols, and also polyester polyols and polycarbonate polyols, castor oil, hydrogenated castor oil, (hy-droxylated epoxidized) soya oil, and also mixtures of the aforementioned polyols.

A small selection of commercially available polyisocyanates would include tetramethylene 1,4-diisocyanate, 2-methylpentamethylene 1,5-diisocyanate, hexamethylene 1,6-diisocyanate (HDI), 2,2,4- and 2,4,4-trimethylhexamethylene 1,6-diisocyanate (TMDI), dodecamethylene 1,12-diisocyanate, lysine diisocyanate and lysine ester diisocyanate, 1-isocyanato-3,3,5-trimethyl-5-isocyanatomethylcyclohexane (isophorone diisocyanate-IPDI), 1,4-diisocyanato-2,2,6-trimethylcyclohexane (TMCDI), 2,2'-, 2,4'- and 4,4'-di-cyclohexylmethane diisocyanate ($H_{12}$MDI), cyclohexane 1,3-diisocyanate and cyclohexane 1,4-diisocyanate (CHDI), 1,3- and 1,4-bis(isocyanatomethyl)cyclohexane, 4,4'-diisocyanatodicyclohexyl-2,2-propane, m- and p-phenylene diisocyanate, 2,3,5,6-tetramethyl-1,4-diisocyanatobenzene, 3,3'-dimethyl-4,4'-diisocyanatodiphenyl (TODD, 2,4- and 2,6-tolylene diisocyanate (TDI), 2,2'-, 2,4'- and 4,4'-diphenylmethane diisocyanate (MDI), naphthalene 1,2-diisocyanate and naphthalene 1,5-diisocyanate (NDI), m- and p-xylylene diisocyanate (XDI), tetramethylxylylene diisocyanate (TMXDI), HDI trimer, polymeric MDI, and mixtures thereof.

From another perspective, R can be defined as being selected from straight-chain, branched or cyclic $C_{2-22}$-alkylene groups, $C_{6-20}$-arylene groups, $C_{6-20}$-alkarylene groups, polyether groups, polycarbonate groups, polyester groups, poly(meth)acrylate groups, and combinations thereof.

The present invention furthermore provides a process for the preparation of a 2-oxo-1,3-dioxolane-4-carboxamide according to the invention, characterized in that 2-oxo-1,3-dioxolane-4-carboxylic acid of formula (II)

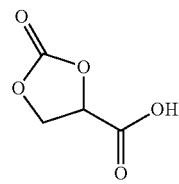

(II)

is reacted with a polyisocyanate of the formula R(NCO)$_n$, where R and n have the meanings given.

Having regard to the formula R(NCO)$_n$ of the polyisocyanate, it is clear that a maximum of (n−1) —NCO groups can be used up in that reaction in order to yield a 2-oxo-1,3-dioxolane-4-carboxamide of formula (I).

According to a preferred embodiment of the process of the invention, this reaction is carried out in the presence of a catalyst selected from tertiary amines, organometallic compounds, and mixtures thereof.

Preferred catalysts are selected from dimethylcyclohexylamine, 4-dimethylaminopyridine (DMAP), diazabicyclooctane (DABCO), diazabicycloundecene (DBU), dibutyltin dilaurate (DBTL), a bismuth carboxylate such as bismuth octanoate or bismuth neodecanoate, a titanium or zirconium alkoxylate or carboxylate, and mixtures thereof.

Moreover, the present invention provides for the use of a 2-oxo-1,3-dioxolane-4-carboxamide for the preparation of a 2-oxo-1,3-dioxolane-4-carboxamide-substituted prepolymer (i.e. a binder). Due to the possible selection of commercially available polyisocyanates and polyols a large number of such binders (prepolymers) can be prepared which, in turn, can be cured e.g. with commercially available amine hardeners.

Finally, the present invention provides said 2-oxo-1,3-dioxolane-4-carboxamide-substituted prepolymer thus obtainable.

The subject invention is now illustrated in more detail by reference to the examples hereinbelow. Chemical shifts are given in ppm.

EXAMPLE 1

Preparation of 4-methoxycarbonyl-2-oxo-1,3-dioxolane (Reference)

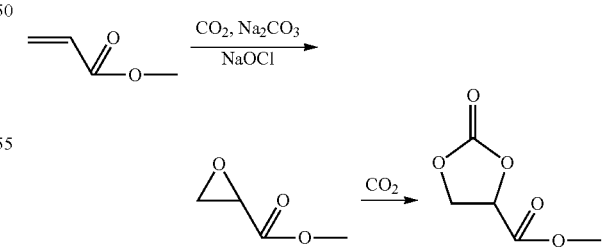

80 g of sodium carbonate were dissolved in 200 ml of distilled water in a 1000 ml three-neck flask. The solution was cooled to 10° C. 58.5 g of methyl acrylate were then added and, after ca. 10 minutes, likewise at 10° C, 400 ml of a 7% strength aqueous sodium hypochlorite solution were stirred in. Then, the system was immediately flushed intensively with $CO_2$. The temperature was allowed to increase to room temperature. The flask was flushed intensively with $CO_2$ for a further 1 h at ca. 25 to 30° C, during which the temperature was held in the stated range by means of occasional cooling with an ice bath. The resulting white solid was filtered off via a suction filter. The filtrate was extracted with 4×90 ml of dichloromethane. The combined organic phase was dried with sodium sulphate and filtered off. The filtrate was removed on a rotary evaporator. Methyl epoxypropionate was obtained in 50 to 60% yield and a purity of 97%.

20 g of the methyl epoxypropionate were mixed with 20 g of tert-butyl methyl ether and 1 g of tetrabutylammonium bromide. The homogeneous mixture was transferred to a 100 ml pressurized reactor and carboxylated for 4 days at 40° C. and a $CO_2$ pressure of 20 bar. After the carboxylation, a two-phase system was obtained; the upper phase consisted of tert-butyl methyl ether, and the lower phase consisted of 4-methoxycarbonyl-2-oxo-1,3-dioxolane (purity 94% (GC), yield 94%).

The product was characterized as follows: $^1$H NMR (500 MHz, $CDCl_3$): 3.82 (3H, s, $CH_3$), 4.50 (1H, dd, J=5.5, 9.0, $CH_2$), 4.66 (1H, dd, J=9.0, 9.0, $CH_2$), 5.09 (1H, dd, J=9.0, 5.5, CH); $^{13}$C NMR (125 MHz, $CDCl_3$): 53.81 ($CH_3$), 67.00 ($CH_2$), 72.34 (CH), 153.97 (—O—CO—O—), 167.42 (—CO—O—); IR (neat): 1812 cm$^{-1}$, (—O—CO—O—), 1742 cm$^{-1}$ (—CO—O—).

EXAMPLE 2

Preparation of 4-methoxycarbonyl-2-oxo-1,3-dioxolane (Reference)

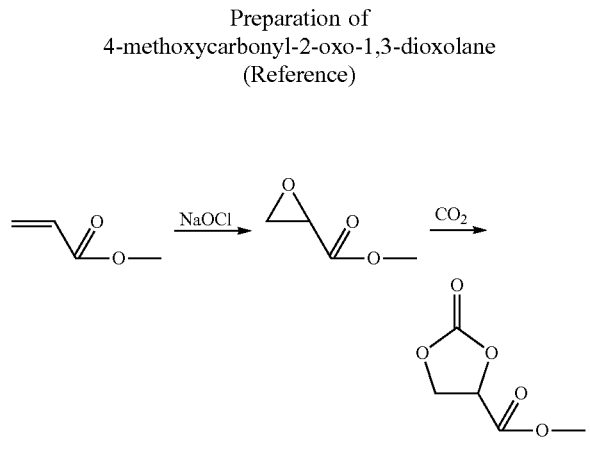

940 ml of a 7% strength aqueous sodium hypochlorite solution were introduced as initial charge in a 2000 ml three-neck flask. The solution was cooled to 0° C. with the help of an ice/salt water bath. 58.5 g of methyl acrylate were then added and the mixture was held at 0° C. for 30 minutes. The low-temperature mixture was then removed and further stirred for ca. 1.5 h such that the mixture heated up by itself (65-70° C.). A colourless, cloudy solution was formed. Then, the solution was cooled to room temperature and extracted with 4×150 ml of dichloromethane. The combined organic phase was dried with magnesium sulphate and filtered off. The filtrate was removed on a rotary evaporator. Methyl epoxypropionate was obtained in 70 to 80% yield and a purity of 97%. The further reaction to give 4-methoxycarbonyl-2-oxo-1,3-dioxolane proceeded as described in Example 1.

EXAMPLE 3

Preparation of 4-methoxycarbonyl-2-oxo-1,3-dioxolane (Reference)

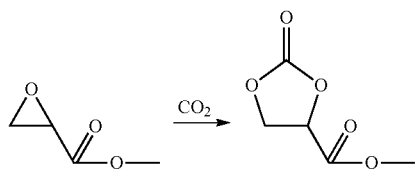

20 g of methyl epoxypropionate were mixed with 20 g of acetonitrile, 1.5 g of benzyltrimethylammonium chloride and 1.5 g of $ZnBr_2$. The homogeneous mixture was transferred to a 100 ml pressurized reactor and carboxylated for 6 days at 25° C. and a $CO_2$ pressure of 30 bar. After the carboxylation, the mixture was diluted with 100 g of acetonitrile. The mixture was purified with aluminium oxide and activated carbon. Then, the acetonitrile was distilled off. This gave 4-methoxycarbonyl-2-oxo-1,3-dioxolane (purity 72% (GC), yield 65%).

EXAMPLE 4

Preparation of 4-methoxycarbonyl-2-oxo-1,3-dioxolane (Reference)

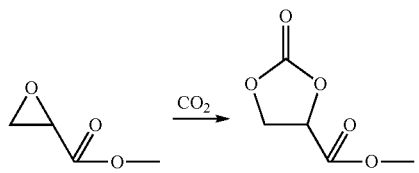

20 g of methyl epoxypropionate were mixed with 20 g of tert-butyl methyl ether, 1.5 g of tetrabutylammonium bromide and 1.5 g of potassium iodide. The homogeneous mixture was transferred to a 100 ml pressurized reactor and carboxylated for 6 days at 50° C. and a $CO_2$ pressure of 30 bar. After the carboxylation, a two-phase system was obtained; the upper phase consisted of tert-butyl methyl ether, and the lower phase consisted of 4-methoxycarbonyl-2-oxo-1,3-dioxolane (purity 83% (GC), yield 79%).

EXAMPLE 5

Acidic hydrolysis of 4-methoxycarbonyl-2-oxo-1,3-dioxolane (Reference)

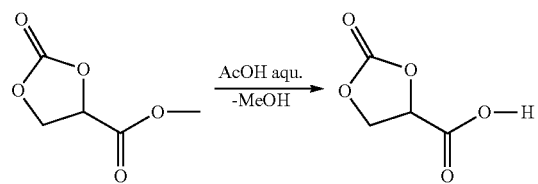

73 g (0.5 mol) of 4-methoxycarbonyl-2-oxo-1,3-dioxolane were heated under reflux for 3 hours with 11 g (0.55 mol) of water and 48 g (0.8 mol) of acetic acid. The mixture was then added to cyclohexane, the separated-off oil was carefully freed from all volatile constituents and the residue was ground with methylene chloride until a colourless crystalline precipitate had formed. The precipitate was washed with diethyl ether and dried in vacuo. This gave 2-oxo-1,3-dioxolane-4-carboxylic acid.

m.p.: 119-121° C. $^1$H-NMR (CDCl$_3$/DMSO-d6 (1/0.1 [mol/mol])): 9.486 (broad, s; 1H); 5.012 (dd; 1H); 4.637 (t; 1H); 4.506 (dd; 1H). $^{13}$C-NMR (CDCl$_3$/DMSO-d6 (1/0.1 [mol/mol])): 168.425 (CO acid); 153.348 (CO cyclocarbonate); 72.247 (CH—COOH); 66.988 (CH$_2$CH—COOH). IR (v [cm$^{-1}$]): 2977 bs (OH acid), 2751 bw, 2658 bw, 2621 bw, 2538 bw, 2407 bw, 1785 bm (CO cyclocarbonate), 1793 bs (CO acid), 1546 w, 1481 w, 1431 w, 1399 s, 1345 w, 1325 w, 128 m, 1196 s, 1087 s, 1074 s, 1039 m, 928 w, 832 s, 769 s, 724 m, 699 s, 650 m, 633 s, 525 s.

EXAMPLE 6

N-Oxide-Mediated Oxidation of Glycerol Carbonate (Reference)

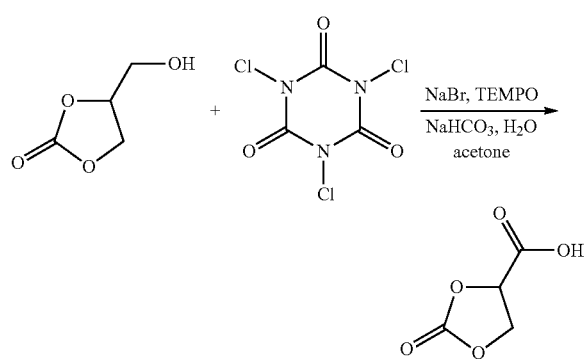

(Procedure analogous to JOC 2003; 68; pages 4999 ff.) 118.1 g (1 mol) of glycerol carbonate, 168 g (2 mol) of sodium hydrogencarbonate, 232 g (1 mol) of trichloroisocya-nuric acid, 18 g (1 mol) of water, 1.5 g (0.01 mol) of TEMPO (2,2,6,6-tetramethylpiperidin-1-oxyl) and 5 g (0.05 mol) of NaBr were introduced as initial charge in 1.5 l of acetone at 0° C. with stirring. The mixture was left to warm to room temperature and stirred for a further 12 hours, after which it was filtered off. The filtrate was concentrated by evaporation. The resulting oil was heated at reflux with chloroform. This gave 2-oxo-1,3-dioxolane-4-carboxylic acid in 97% yield.

EXAMPLE 7

Aerobic Oxidation of Glycerol Carbonate (Reference)

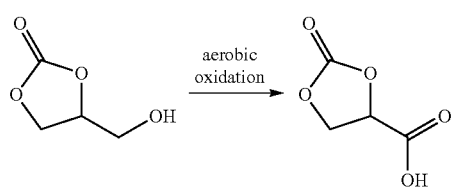 [SMILES: O=C1OCC(CO)O1 ; O=C1OCC(C(=O)O)O1]

118 g (1 mol) of glycerol carbonate (4-(hydroxymethyl)-2-oxo-1,3-dioxolane), 16.3 g (0.1 mol) of N-hydroxyphthalimide, 7.8 g (0.045 mol) of m-chlorobenzoic acid and 1.3 g (0.05 mol) of cobalt(II) acetylacetonate were dissolved in 300 ml of glacial acetic acid and 1 l of ethyl acetate. The solution was saturated with oxygen and heated at reflux for 6 hours under an oxygen atmosphere. All volatile constituents were distilled off and the residue was ground with diethyl ether. Insoluble constituents were removed by means of washing with dichloromethane and toluene. This gave 2-oxo-1,3-dioxolane-4-carboxylic acid. The yield was about 15%.

EXAMPLE 8

Aerobic Oxidation of Glycerol Carbonate (Reference)

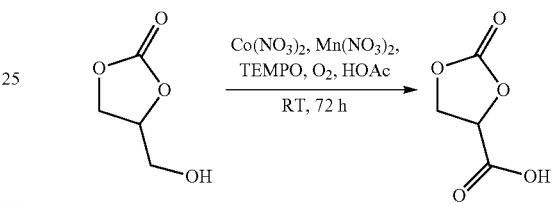

11.81 g (0.1 mol) of glycerol carbonate (4-(hydroxymethyl)-2-oxo-1,3-dioxolane), 0.50 g (0.002 mol) of manganese(II) nitrate tetrahydrate (Mn(NO$_3$)$_2$.4 H$_2$O), 0.58 g (0.002 mol) of cobalt(II) nitrate hexahydrate (Co(NO$_3$)$_2$.6 H$_2$O) and 1.88 g (0.012 mol) of TEMPO (2,2,6,6-tetramethylpiperidin-1-oxyl) were dissolved in 100 ml of acetic acid. The reddish solution was stirred for 72 hours at room temperature under an oxygen atmosphere, evaporated to dryness, and the crude product was purified by recrystallization. This gave 2-oxo-1,3-dioxolane-4-carboxylic acid in the form of white to yellowish crystal needles. The yield was about 75%, and the analytical data were in agreement with the known data (Example 5).

EXAMPLE 9

Reaction of 2-oxo-1,3-dioxolane-4-carboxylic acid with IPDI

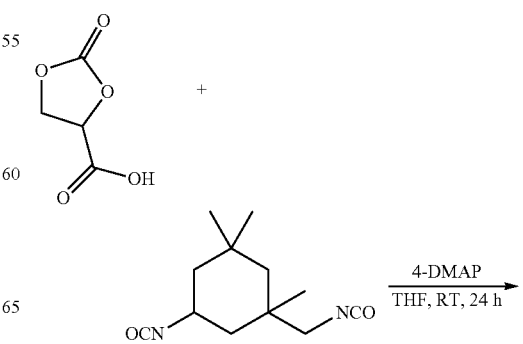

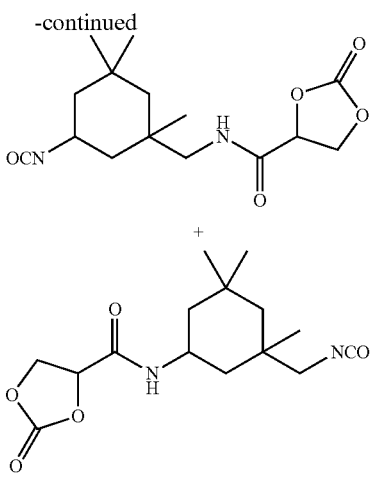

A 2-oxo-1,3-dioxolane-4-carboxamide building block on the basis of isophorone diisocyanate (IPDI) was prepared. Under an atmosphere of dry nitrogen, 3.33 g isophorone diisocyanate (IPDI) (0.015 mol) and 0.018 g (1 mol-%) 4-DMAP were dissolved in 10 ml of dry THF. 2.0 g 2-Oxo-[1,3]dioxolane-4-carboxylic acid (0.015 mol) was dissolved in 40 ml of dry THF and slowly added to the mixture via a dropping funnel. The reaction was stirred at room temperature for 24 h after which the solvent was evaporated and the product was obtained as yellow gel in almost quantitative yield. The gel was recrys-tallized from cyclohexane to give a white powder as a mixture of two isomers.

m.p.=93° C. (dec.); NCO-content: 11.66% (theory: 13.48%); $^1$H-NMR (DMSO-$d_6$): 8.35 (s, 1H, NH), 5.12 (dm, 1H, cyclocarbonate), 4.65 (m, 1H, cyclocarbonate), 4.39 (m, 1H, cyclocarbonate), 3.31 (m, 2H, $CH_2$), 2.89 (m, 1H, CH), 1.61-0.70 (m, 15H, alkyl-$CH_2$ and —$CH_3$); $^{13}$C-NMR (DMSO-$d_6$): 167.4 (CON), 165.9 (CON'), 154.4 (OC(O)O), 122.3 (NCO), 73.3 (CH-cyclocarbonate), 67.4 ($CH_2$-cyclocarbonate), 52.2 (alkyl-$CH_2$), 46.6 (alkyl-$CH_2$), 44.8 ($CH_2$—N), 42.2 (alkyl-$CH_2$), 36.1 (CH—N), 34.8 ($CH_3$), 31.3 ($CH_3$), 27.3 ($CH_3$), 25.1 ($C_{quart.}$-$Me_2$), 22.9 ($C_{quart.}$—$CH_2$—N) ppm; IR (v [$cm^{-1}$]): 3316 (m, NH), 2954 (m), 2925 (m), 2874 (m), 2253 (s, NCO), 1812 (s, CO-cyclocarbonate), 1790 (s, CO-cyclocarbonate), 1671 (s, CO-amide), 1546 (s, C—N), 1462 (w), 1366 (m), 1304 (w), 1241 (w), 1156 (s), 1062 (s), 895 (w), 857 (w), 767 (m), 729 (w), 577 (m), 470 (w), 432 (w).

EXAMPLE 10

Reaction of Building Block with Polypropylene Glycol

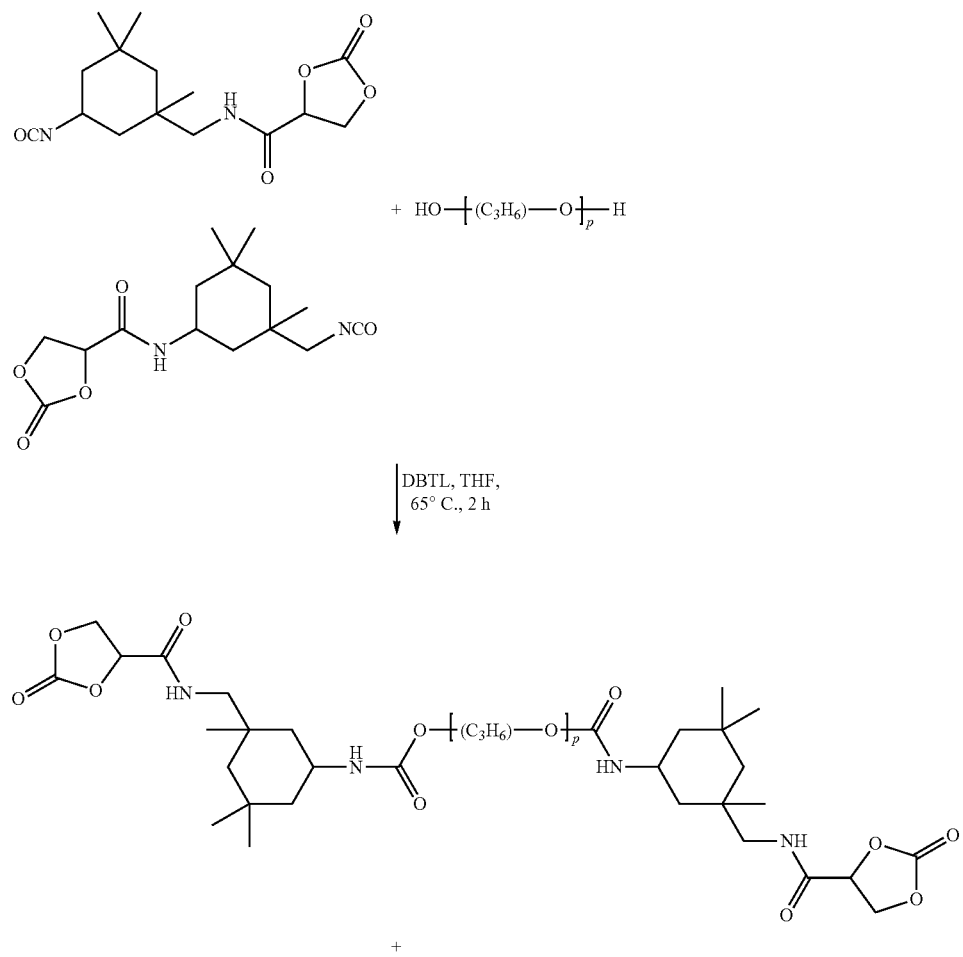

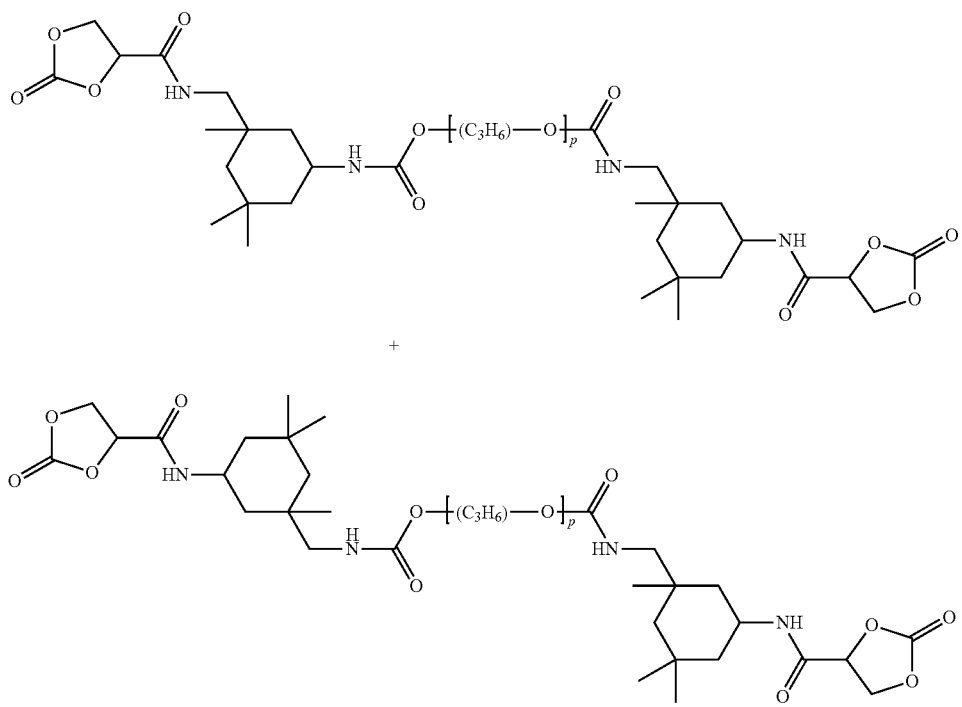

In the presence of DBTL (1 mol %), the resulting mixture of Example 9 could be reacted with Lupranol® 1000 to give a difunctional prepolymer. Thus, 7.76 g (0.025 mol) of the product of Example 9 was dissolved in dry THF and 24.61 g Lupranol® 1000 (polypropylene glycol of BASF SE; 0.012 mol) and 0.10 g DBTL (0.16 mmol) was added and the reaction mixture was heated to 65° C. for 2 h. After evaporation of the solvent, the product was obtained as yellowish to orange, slightly turbid oil as a mixture of isomers.

The IR spectrum was almost identical with the IR spectrum of a of prepolymer prepared from Lupranol® 1000, IPDI, and 2-oxo-1,3-dioxolane-4-carboxylic acid via direct prepolymer synthesis. Both products formed sticky, jellylike products when cured with amines (IPDA, TMD, tris(aminoethyl)amine, and the like).

EXAMPLE 11

Reaction of 2-oxo-1,3-dioxolane-4-carboxylic acid with TDI

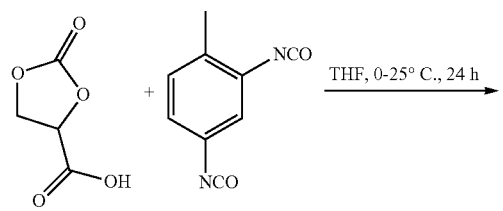

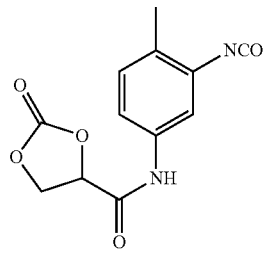

A 2-oxo-1,3-dioxolane-4-carboxamide building block on the basis of toluene-2,4-diisocyanate (TDI) was prepared. Under an atmosphere of dry nitrogen, 6.97 g toluene-2,4-diisocyanate (0.04 mol) and 5.28 g 2-oxo-[1,3]-dioxolane-4-carboxylic acid (0.04 mol) were dissolved in 50 ml of dry THF and stirred at 0° C. for 24 h. After evaporation of the solvent, the product was obtained as yellowish, waxy solid in almost quantitative yield.

m.p.=109-111° C. (dec.); NCO-content: 15.70% (theory: 16.02%); $^1$H-NMR (DMSO-$d_6$): 10.49 (s, 1H, NH), 7.52-7.11 (m, 3H, Ar), 5.27 (m, 1H, cyclocarbonate), 4.71 (m, 1H, cyclocarbonate), 4.55 (m, 1H, cyclocarbonate), 2.24 (m, 3H, CH$_3$). $^{13}$C-NMR (THF-$d_8$): 166.9 (NHC(O)O), 154.4 (OC(O)O), 138.2, 133.6, 131.5, 129.6 (Ar), 126.1 (NCO), 118.5, 117.5 (Ar), 74.6 (CH-cyclocarbonate), 68.0 (CH$_2$-cyclocarbonate), 17.8 (CH$_3$).

EXAMPLE 12

Reaction of 2-oxo-1,3-dioxolane-4-carboxylic acid with TDI

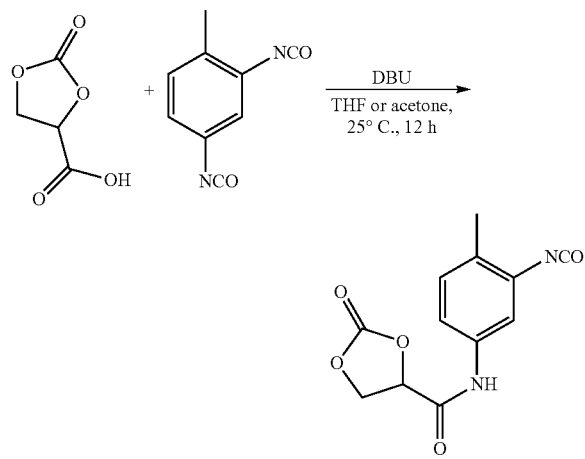

Under an atmosphere of dry nitrogen, 13.94 g toluene-2,4-diisocyanate (TDI) (0.08 mol) and 10.56 g 2-oxo-[1,3]-dioxolane-4-carboxylic acid (0.08 mol) were dissolved in 70 ml of dry THF or acetone. 0.12 g (1 mol %) of 1,8-diazabicyclo[5.4.0]-undec-7-ene (DBU) were added and the reaction mixture was stirred at ambient temperature for 12 h. After evaporation of the solvent, the product was obtained as white solid in quantitative yield.

Analytic data is in good agreement with the data given above. The reaction can also be performed in dry acetonitrile with 4-DMAP as a catalyst.

EXAMPLE 13

Reaction of Building Block with Hexane-1,6-Diol

In the presence of DBTL (0.02 wt.-%), the resulting product of Example 11 or 12 could be reacted with hexane-1,6-diol to give a difunctional prepolymer. Thus, 5.0 g (0.019 mol) of said product was dissolved in dry THF and 1.13 g hexane-1,6-diol (9.53 mmol) and 1.2 mg DBTL (0.002 mmol) were added. The reaction mixture was heated to 60° C. for 4 h. After evaporation of the solvent, the product was obtained as yellowish to brownish powder.

$^1$H-NMR (DMSO-$d_6$): 10.42 (s, 2H, NH-amide), 8.83 (s, 2H, NH-urethane), 7.78-7.11 (m, 3H, Ar), 5.29 (m, 1H, cyclocarbonate-CH), 4.71 (m, 1H, cyclocarbonate-CH$_2$), 4.56 (m, 1H, cyclocarbonate-CH$_2$'), 4.07 (4H, m, CH$_2$—O), 2.17 (m, 3H, CH$_3$), 1.63 (m, 4H, CH$_2$-hexyl), 1.40 (4H, m, CH$_2$-hexyl).

The resulting bifunctional binder can be cured with different amines such as Lupasol FG® (BASF SE), Polyetheramine T 403 or IPDA to give cured products. Curing time and film properties depend on the amine structure and can be tuned between several seconds (Lupasol FG) and several hours (T 403). Film properties vary from hard and brittle (Lupasol FG) to soft and elastic (T 403).

EXAMPLE 14

Reaction of 2-oxo-1,3-dioxolane-4-carboxylic acid with Desmodur N3600

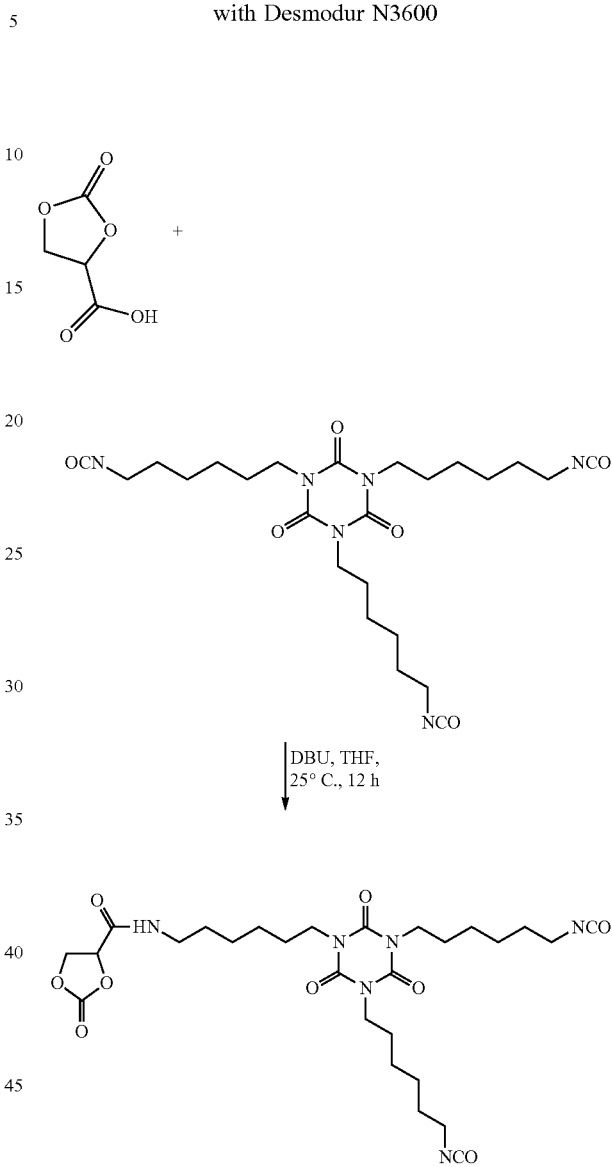

A 2-oxo-1,3-dioxolane-4-carboxamide building block on the basis of Desmodur N 3600 (HDI-Trimer, Bayer AG, 23% NCO) containing one cyclic carbonate functionality was prepared.

Under an atmosphere of dry nitrogen, 15.0 g Desmodur N 3600 (0.082 mol NCO), 3.61 g 2-oxo-[1,3]-dioxolane-4-carboxylic acid (0.027 mol) and 0.04 g DBU were dissolved in 50 ml of dry THF and stirred at 25° C. for 12 h. After evaporation of the solvent, the product was obtained as colorless oil in quantitative yield.

NCO-content: 11.3% (theory: 14.2%); $^1$H-NMR (THF-$d_8$): 7.79 (s, 1H, NH), 5.02 (m, 1H, cyclocarbonate), 4.65 (m, 1H, cyclocarbonate), 4.49 (m, 1H, cyclocarbonate), 3.87 (m, 6H, 3×CH$_2$—N), 3.34 (t, 4H, 2×CH$_2$—NCO), 3.26 (m, 2H, CH$_2$—N-amide), 1.67-1.37 (m, 24H, 12×CH$_2$) ppm.

EXAMPLE 15

Reaction of 2-oxo-1,3-dioxolane-4-carboxylic acid with Desmodur N3600

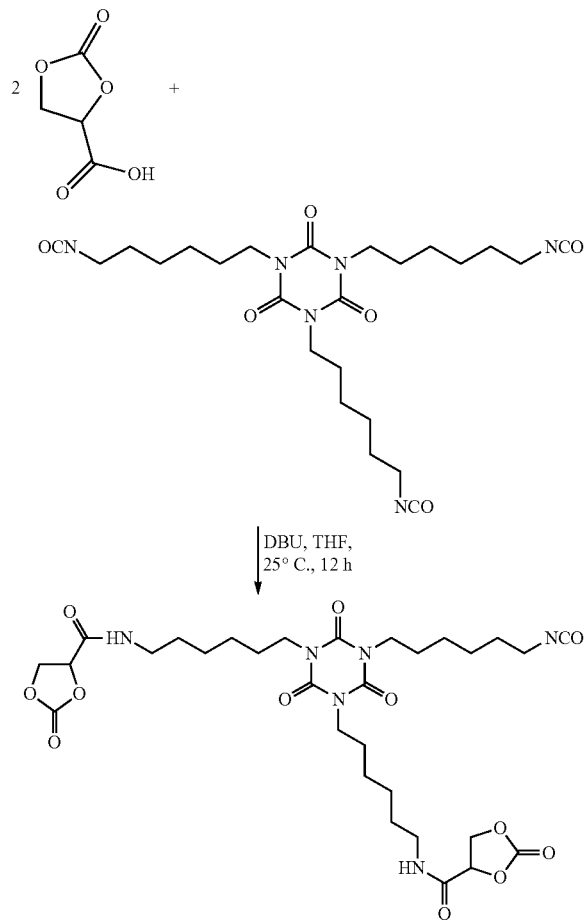

A 2-oxo-1,3-dioxolane-4-carboxamide building block on the basis of Desmodur N 3600 (HDI-trimer, Bayer AG) containing two cyclic carbonate functionalities was prepared analogously.

Under an atmosphere of dry nitrogen, 15.0 g N 3600 (0.082 mol NCO), 7.23 g 2-oxo-[1,3]-dioxolane-4-carboxylic acid (0.055 mol) and 0.08 g DBU were dissolved in 60 ml of dry THF and stirred at 25° C. for 12 h. After evaporation of the solvent, the product was obtained as colorless viscous oil in quantitative yield.

NCO-content: 4.3% (theory: 6.2%); $^1$H-NMR (THF-d$_8$): 7.81 (s, 2H, NH), 5.05 (m, 2H, cyclocarbonate), 4.67 (m, 2H, cyclocarbonate), 4.50 (m, 2H, cyclocarbonate), 3.85 (m, 6H, 3×CH$_2$—N), 3.34 (t, 2H, CH$_2$—NCO), 3.26 (m, 4H, CH$_2$—N-amide), 1.67-1.37 (m, 24H, 12×CH$_2$) ppm.

In both cases, the free isocyanate group can be used for the preparation of oligo-functional binders via reaction with a di- or polyol.

The invention claimed is:

1. 2-Oxo-1,3-dioxolane-4-carboxamide of formula (I),

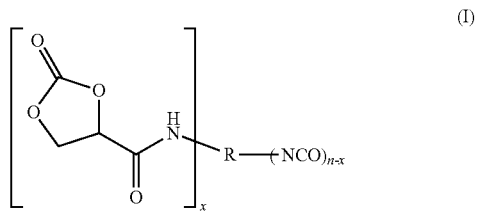

wherein R is a radical having a valency n of 2 to 4 and x is an integer from 1 to an amount equal to the valency n minus 1.

2. 2-Oxo-1,3-dioxolane-4-carboxamide according to claim 1, wherein the radical has a valency n from 2 to 3.

3. 2-Oxo-1,3-dioxolane-4-carboxamide according to claim 1, wherein R is selected from straight-chain, branched or cyclic C$_{2-22}$-alkylene groups, C$_{6-20}$-arylene groups, C$_{6-20}$-alkarylene groups, polyether groups, polycarbonate groups, polyester groups, and poly(meth)acrylate groups.

4. A process for the preparation of a 2-oxo-1,3-dioxolane-4-carboxamide as defined in claim 1, characterized in that 2-oxo-1,3-dioxolane-4-carboxylic acid of formula (II)

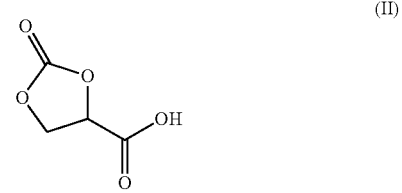

is reacted with a polyisocyanate of the formula R(NCO)$_n$, where R is a radical having a valency n of 2 to 4.

5. The process according to claim 4, characterized in that the reaction is carried out in the presence of a catalyst selected from tertiary amines, organometallic compounds, and mixtures thereof.

6. The process according to claim 5, characterized in that the catalyst is selected from dimethylcyclohexylamine, 4-dimethylaminopyridine (DMAP), diazabicyclo-octane (DABCO), diazabicycloundecene (DBU), dibutyltin dilaurate (DBTL), a bismuth carboxylate, bismuth octanoate, bismuth neodecanoate, a titanium alkoxylate, a titanium carboxylate, a zirconium alkoxylate, a zirconium carboxylate, and mixtures thereof.

7. A method comprising reacting the 2-oxo-1,3-dioxolane-4-carboxamide as defined in claim 1 with a polyol for the preparation of a 2-oxo-1,3-dioxolane-4-carboxamide-substituted prepolymer.

8. The 2-oxo-1,3-dioxolane-4-carboxamide-substituted prepolymer obtained according to claim 7.

* * * * *